United States Patent [19]

Yamamoto et al.

[11] Patent Number: 5,032,793
[45] Date of Patent: Jul. 16, 1991

[54] NMR GATED IMAGING APPARATUS

[75] Inventors: Etsuji Yamamoto, Akishima; Hiroshi Kanda, Tokorozawa; Hideki Kohno, Tama, all of Japan

[73] Assignee: Hitachi, Ltd., Tokyo, Japan

[21] Appl. No.: 478,739

[22] Filed: Feb. 9, 1990

Related U.S. Application Data

[63] Continuation of Ser. No. 328,457, Mar. 24, 1989, abandoned.

[30] Foreign Application Priority Data

Mar. 25, 1988 [JP] Japan .................................. 63-69422
Sep. 19, 1988 [JP] Japan ................................. 63-232362

[51] Int. Cl.$^5$ .............................................. G01V 3/00
[52] U.S. Cl. .................................................. 324/309
[58] Field of Search ................ 324/309, 307, 312, 318; 128/653 A, 653 AF, 653 SC

[56] References Cited

U.S. PATENT DOCUMENTS

| | | | |
|---|---|---|---|
| 4,694,836 | 9/1987 | Buikman et al. | 324/309 |
| 4,739,766 | 4/1988 | Riederer | 324/309 |
| 4,802,988 | 4/1989 | Crooks et al. | 324/318 |

Primary Examiner—Hezron E. Williams
Assistant Examiner—Louis M. Arana
Attorney, Agent, or Firm—Antonelli, Terry, Stout & Kraus

[57] ABSTRACT

Disclosed is an NMR gated imaging apparatus in which an ultrasonic pulse signal is repeatedly transmitted toward the heart of a human body from an ultrasonic transducer to detect the position of the heart on the basis of the time of detection of a peak of an echo signal, and excitation and measurement of an NMR signal are executed only when a peak detector generates a detection output signal having a level included in a predetermined range. Thus, the NMR signal is repeatedly measured according to a programmable phase encoding amount at a limited phase of gated imaging.

8 Claims, 5 Drawing Sheets

FIG. 3A TRANSMITTING PULSE
FIG. 3B DETECTED RECEIVING SIGNAL
FIG. 3C TIME GATE
FIG. 3D PEAK DETECTION
FIG. 3E COUNTER

FIG. 5E NMR SIGNAL

NMR GATED IMAGING APPARATUS

This application is a continuation application Ser. No. 328,457, filed Mar. 24, 1989, now abandoned.

BACKGROUND OF THE INVENTION

This invention relates to an imaging apparatus and method utilizing nuclear magnetic resonance (abbreviated hereinafter as NMR) for imaging, and more particularly to an imaging apparatus of the kind described above which is suitable for imaging a moving region of an object with high accuracy.

In an imaging apparatus utilizing the phenomenon of NMR, echo signals from various positions of an object must be separated and discriminated from one another. According to one of methods employed hitherto, a field gradient is applied to a magnetic field in which an object is placed, and different resonance frequencies or phase encoding amounts are based to derive position information. Such a method is described in, for example, U.S. Pat. No. 4,506,222. In the method described in this U.S. patent, excitation and measurement of a plurality of NMR signals derived from a living body in response to application of phase-encoding field gradients having different amplitudes are required so as to obtain one tomographic image. Therefore, the total length of time required for the measurement becomes necessarily long as compared to the cardiac cycle in the living body.

On the other hand, a gated imaging method is also known which is proposed to prevent blurring of an image due to the cardiac action or breathing of a living body. For example, a technique of gated imaging in X-rays computer tomography is described in U.S. Pat. No. 3,952,201. Also, JP-A-62-44231 (1987) proposes a method of cardiac action or breathing gated imaging in an NMR imaging apparatus. In these publications, the cardiac action was indirectly measured by means of electric cardiography.

SUMMARY OF THE INVENTION

In the case of the prior art method and apparatus designed for gated imaging based on the output of an electric cardiograph, complete correspondence between the gated output of the electric cardiograph and the actual motion of the heart of the living body has not always been attained. As a result, there has been the tendency of degradation of the image quality due to a gating error which may occur during imaging. Further, because a quickly changing field gradient or a pulsating RF magnetic field is applied in the NMR imaging apparatus, there has been the problem that the output of the electric cardiograph tends to be adversely affected by the applied field gradient or magnetic field.

It is one of objects of the present invention to provide an NMR gated imaging apparatus and method capable of producing an image in accurately gated relation with the motion of a region of interest in an object.

Another object of the present invention is to provide an NMR gated imaging apparatus of the above character which includes gated detecting means capable of detecting the motion of the region of interest in the object without being adversely affected by a field gradient or an RF magnetic field used for imaging.

The NMR gated imaging apparatus of the present invention is featured by comprising ultrasonic position detecting means for repeatedly transmitting ultrasonic pulse wave into an object from the surface of the object, and, on the basis of an echo signal detected each time, generating a position information output signal pertaining to the position of a region of interest in the object, and gating means for permitting excitation and measurement of an NMR signal during the period of time in which the level of the position information signal lies within a predetermined range but inhibiting excitation and measurement of the NMR signal in the other period.

In a typical method, the ultrasonic position detecting means described above measures the position of the region of interest on the basis of the time difference between the time of transmission of an ultrasonic pulse and the time of appearance of a peak in a detection signal of echo wave reflected from the region of interest. In another method, the ultrasonic detecting means detects a Doppler shift of the detection signal of the echo wave reflected from the region of interest, and the time of generation of a specific frequency, that is, the time where the velocity of the region of interest attains a specific value is defined as a specific phase of the periodic motion of the region of interest.

DESCRIPTION OF THE PREFERRED EMBODIMENTS

Preferred embodiments of the present invention will now be described in detail with reference to the drawings.

Figure 1:
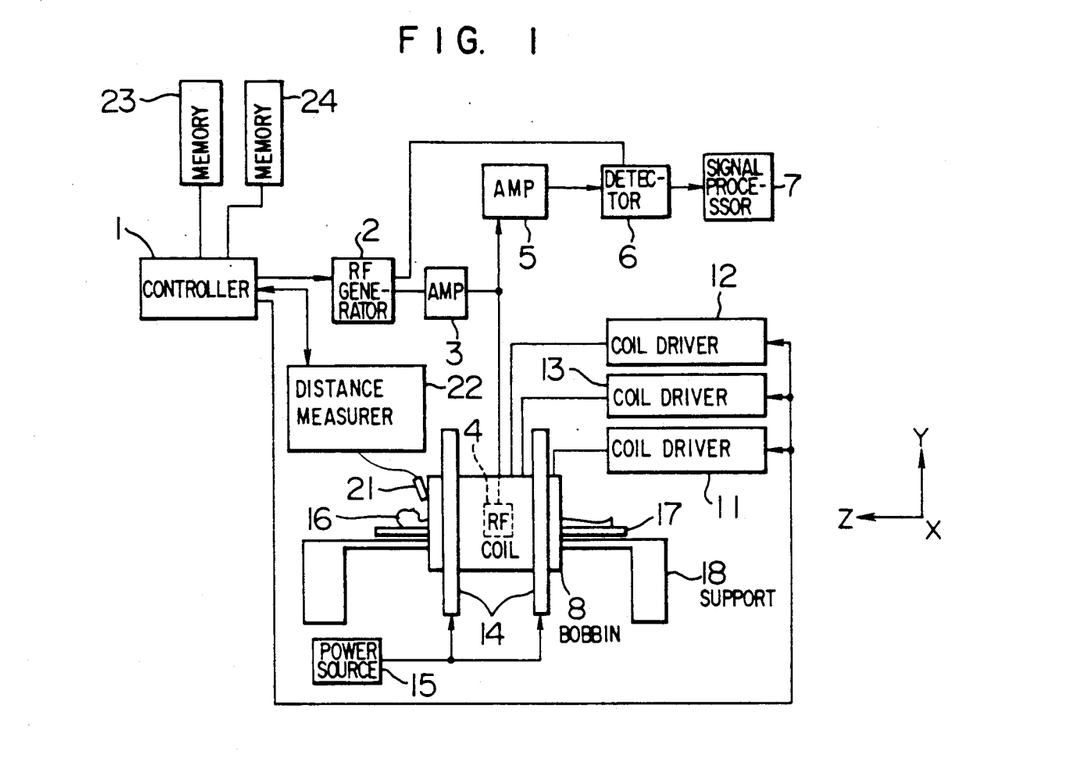
FIG. 1 is a block diagram showing the structure of a preferred embodiment of the NMR gated imaging apparatus according to the present invention.

FIG. 1 shows the structure of an embodiment of the NMR gated imaging apparatus of the present invention. Referring to FIG. 1, a controller 1 generates and applies various instruction signals to controlled components of the apparatus at predetermined timings the output of an RF generator 2 is applied to an RF coil 4 after being amplified by an amplifier 3 so as to drive the RF coil 4. This RF coil 4 acts also as a receiving coil, and signal components received by the RF coil 4 pass through another amplifier 5 to be converted into an image by a signal processor 7 after being detected by a detector 6. The output of the RF generator 2 is also applied to the detector 6 to be used as a reference signal at the time of quadrature detection in the detector 6.

Current is supplied to static magnetic field coils 14 from a power source 15, and the static magnetic field coils 14 produce a static magnetic field which is uniform in a z direction in a space in which an object of measurement is placed. A bobbin 8 described later is disposed inside the static magnetic field coils 14. Three sets of gradient coils are mounted on the bobbin 8 so that the intensity of the magnetic field produced in the space has field gradients in the x, y and z directions respectively. These gradient coils are driven by coil drivers 11, 12 and 13 respectively. The RF coil 4 described above is installed inside the bobbin 8 at a position further inner relative to the static magnetic field coils 14. A human body 16 which is the object of NMR measurement is placed on a bed 17 adapted to move on a support 18.

The apparatus of the present invention differs from the related art apparatus in that an ultrasonic transducer 21, a distance measuring unit 22 and memories 23 and 24 are additionally provided.

Figure 2:
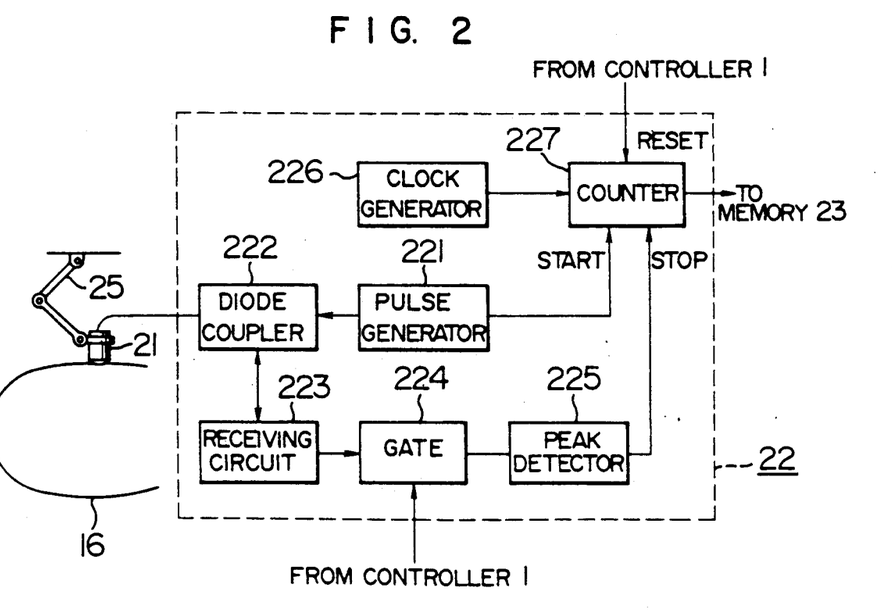
FIG. 2 is a block diagram showing in detail the arrangement and structure of principal parts of the embodiment shown in FIG. 1.

FIG. 2 shows in detail the arrangement of the ultrasonic transducer 21 and the structure of the distance measuring unit 22. Referring to FIG. 2, the ultrasonic transducer 21 is mounted on the free end of a multiple-articulated arm 25. The transducer 21 is fixed so that its signal emitting surface is in contact with the surface of the human body 16 and directed toward a region of interest in the human body 16. Piezoelectric material used in the transducer 21 is, for example, lead zirconate titaniate (PZT) compound. It is more favorable to use a piezoelectric polymer, for example polyvinyliden fluoride, since the piezoelectricity does not change even in high magnetic field. The distance measuring unit 22 includes a pulse generator 221, a diode coupler 222, a receiving circuit 223, a gate 224, a peak detector 225, a clock generator 226 and a counter 227.

A transmitting signal generated from the pulse generator 221 is applied through the diode coupler 222 to the ultrasonic transducer 21, while a receiving signal from the transducer 21 is applied through the diode coupler 222 to the receiving circuit 223. The receiving circuit 223 amplifies the receiving signal, and the amplified output signal is subjected to diode detection. The detected signal is applied through the gate 224 to the peak detector 225. A trigger signal from the pulse generator 221 is connected to a start input terminal of the counter 227, and the detection output signal of the peak detector 225 is connected to a stop input terminal of the counter 227. Therefore, the counter 227 counts a clock signal applied from the clock generator 226 between the time where the transmitting signal is generated from the pulse generator and the time where the peak of the receiving signal is detected by the peak detector 225.

Figure 3A:
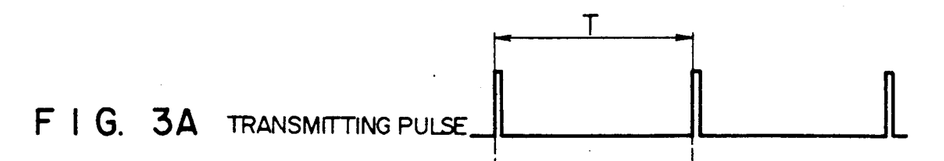
FIGS. 3A to 3E are a time chart showing the operation of various blocks shown in FIG. 2.
Figures 3B, 3C:
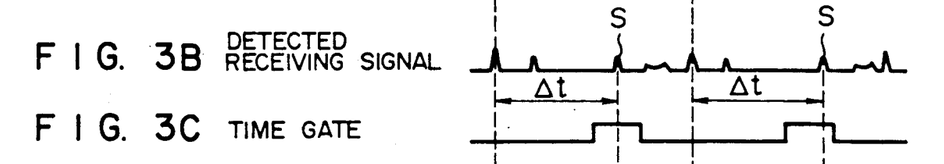
Figures 3D, 3E:
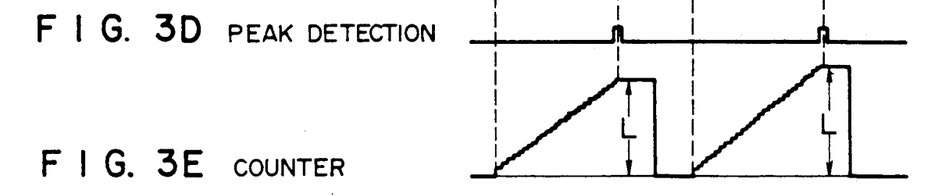

FIG. 3A shows the waveform of the output signal of the pulse generator 221, FIG. 3B shows the waveform of the receiving signal detected by the receiving circuit 223, FIG. 3C shows the pass period of the gate 224, FIG. 3D shows the waveform of the output signal of the peak detector 225, and FIG. 3E shows the count of the counter 227. The pass period of the gate 224 is manually set or determined by a time gate setting signal applied from the controller 1 shown in FIG. 1, so that, among various echo signal components successively detected after transmission of the transmitting signal, an echo signal component S reflected from the region of interest, for example, the wall of the heart of the human body 16, can only be permitted to pass through the gate 224, and passage of other unnecessary echo signal components through the gate 224 can be inhibited. The count of the counter 227, when the counting operation is stopped in response to the application of the peak detection output from the peak detector 225, represents the time difference Δt between the time of transmission of the transmitting signal and the time of detection of the echo signal component S reflected from the region of interest. After the pass period of the gate 224, the count of the counter 227 is read out by the controller 1 shown in FIG. 1 and stored in the memory 23. After the count of the counter 227 is read out, the counter 227 is reset by a reset signal applied from the controller 1 and prepares for measurement of Δt in the next cycle of transmission of the transmitting signal from the pulse generator 221.

The value of the time difference Δt described above represents the distance L between the ultrasonic transducer 21 and the region of interest in the human body 16. The distance L is expressed in terms of Δt as follows:

$$L = \frac{\Delta t \cdot V}{2}$$

where V is the mean velocity of sound in the human body 16. The value of the mean velocity V of sound in the human body 16 is about 1,500 m/sec, and the distance L is about 10 cm when the heart is the region of interest. In this case, therefore, Δt is given by Δt=133 μsec. When now the wave number of the echo wave is 5, and the frequency of the ultrasonic wave is 3 MHz, the wavelength of the echo wave is 2.5 mm. By detecting the position of the peak of the echo signal, the position of the heart can be detected with an error of only about 0.1 mm to 0.2 mm. The pulse repetition period T of the transmitting signal can be set at, for example, 200 μsec which is slightly longer than 133 μsec. Therefore, the distance measuring unit 22 having the structure shown in FIG. 2 can repeatedly measure the position of the heart with the period of 200 μsec.

A practical sequence of steps for imaging will now be described with reference to FIG. 4.

Figure 4:
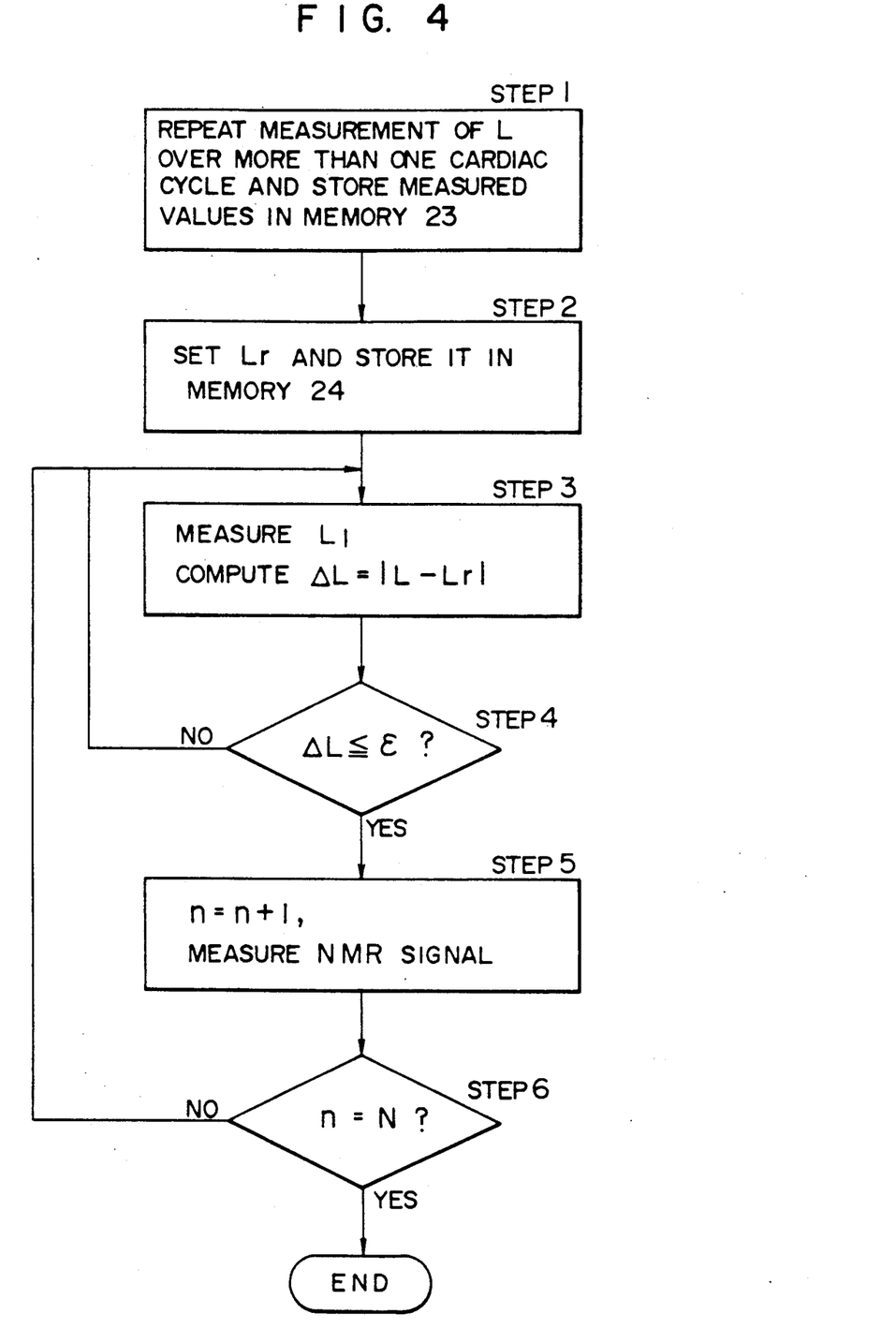
FIG. 4 is a flow chart showing a sequence of steps of measurement in the embodiment shown in FIG. 1.

In a step 1 in FIG. 4, the distance L between the ultrasonic transducer 21 and the heart of the human body 16 is measured for each of a plurality of cardiac cycles. More concretely, the distance measuring unit 22 repeats transmission of the pulse signal with the predetermined period T as shown in FIG. 3A, and the length of time Δt, required until the peak of the echo signal is detected after the transmission of the pulse of the pulse signal in each period, is measured to measure the distance L between the ultrasonic transducer 21 and the heart of the human body 16. The successively measured values of the distance L are stored in the memory 23. Then, in a step 2, the phase of execution of gated imaging, that is, the position of the heart, is selected, and the corresponding distance $L_r$ is stored in the memory 24. In a step 3, the distance L between the ultrasonic transducer 21 and the heart of the human body 16 is measured by the distance measuring unit 22 while transmitting and receiving the ultrasonic wave, and the absolute value of the difference ΔL between the measured value of the distance L and the value of $L_r$ stored in the memory 24 is computed. That is, $\Delta L = |L-L_r|$ is computed. Then, in a step 4, the value of ΔL is compared with a setting ε. When the result of comparison in the step 4 proves that ΔL≦ε, the step 4 is followed by a step 5 in which an NMR signal is measured.

Figure 5A:
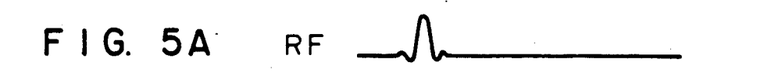
FIGS. 5A to 5E are a time chart showing the NMR measurement sequence in the embodiment shown in FIG. 1.
Figure 5B:
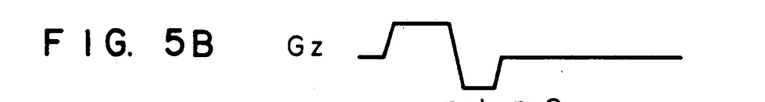
Figure 5C:
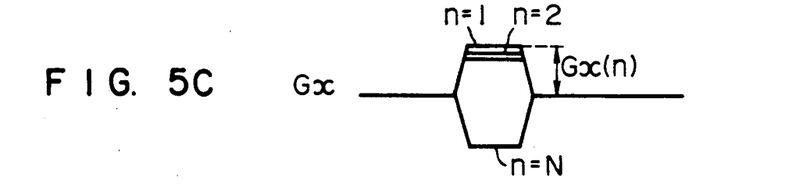
Figures 5D, 5E:
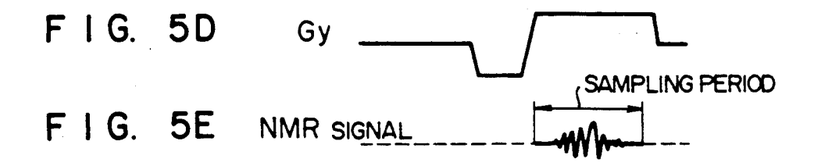

FIGS. 5A to 5D show a sequence of measurement of the NMR signal. In the illustrated embodiment of the present invention, the so-called two-dimensional Fourier transformation is used for imaging. That is, in a state in which a magnetic field gradient $G_z$ as shown in FIG. 5B is applied, an RF magnetic field pulse having a high frequency selectivity as shown in FIG. 5A is applied, thereby selectively exciting nuclear spins existing in a specific slice only. Then, a phase-encoding magnetic field gradient $G_x$ having one of N kinds of programmable amplitudes $G_{x(n)}$ (n=1, 2, ..., N) as shown in FIG. 5C is applied so as to encode the phase of the nuclear spins into the position information of the heart in the x direction. Then, a magnetic field gradient $G_y$ in the y direction as shown in FIG. 5D is applied. The period during which the magnetic field gradient $G_y$ is maintained constant is selected as a sampling period, and, during this sampling period, an NMR signal having a waveform as shown in FIG. 5E is detected from the RF coil 4 and sampled after detection by the detector 6.

The above description refers, by way of example, to acquisition of an NMR image in a slice perpendicular to the z direction. It is apparent that the waveforms of the magnetic field gradients $G_z$, $G_x$ and $G_y$ are interchanged depending on the direction of the slice. In the case of slice in an oblique direction, the waveforms of $G_z$, $G_x$ and $G_y$ are obtained by the combination of the magnetic field gradients.

Returning to FIG. 4, the NMR signal is first measured by setting the value of n in the magnetic field gradient $G_{x(n)}$ at n=1. After this first measurement of the NMR signal, the step 5 is followed by a step 6 in which decision is made as to whether or not n is equal to N (n=N). When the result of the decision in the step 6 is "No", the step 6 is followed by the step 3 in which the distance L is measured again by transmission and reception of the ultrasonic wave, and the difference $\Delta L$ is computed again. On the other hand, when the result of comparison in the step 4 proves that $\Delta L > \epsilon$, the step 4 is not followed by the step 5 but followed by the step 3 again. In the manner described above, measurement of the NMR signal is executed while successively incrementing the value of n, that is, while successively changing the amplitude of the phase-encoding magnetic field gradient $G_x$. When the result of decision in the step 6 proves that n=N, the series of measurement steps for obtaining one tomographic image ends. That is, the NMR signal is excited and measured N times only when the position of the heart is way close to a pre-set position. Therefore, a tomographic image substantially completely free from blurring attributable to, for example, the cardiac action can be obtained.

Figure 6:
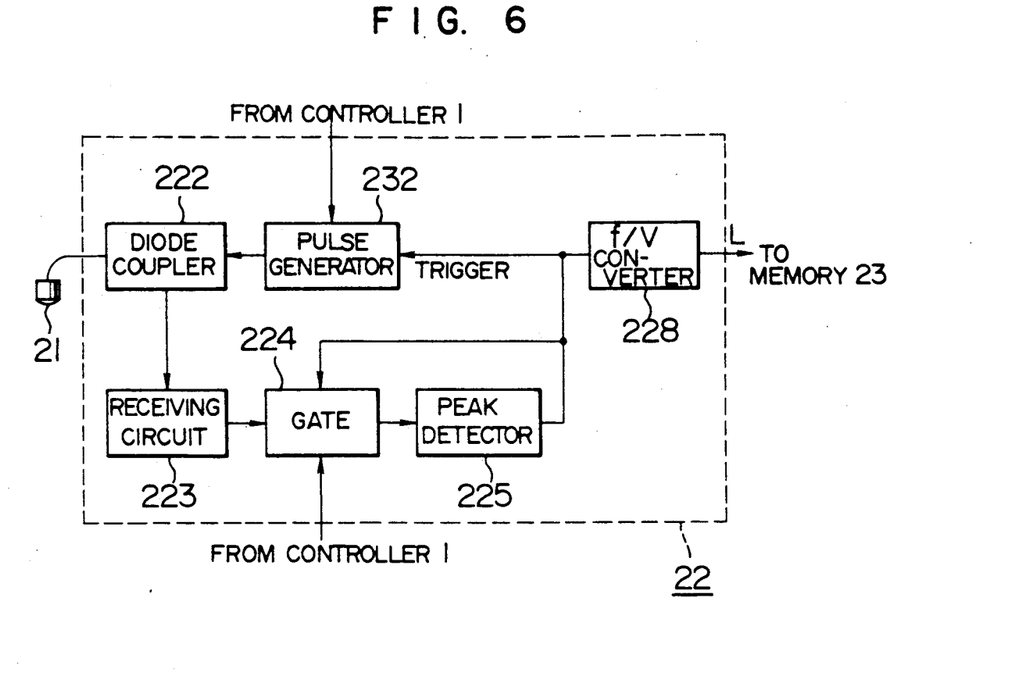
FIGS. 6 and 7 are block diagrams showing in detail the arrangement and structure of principal parts of other embodiments of the present invention respectively.

FIG. 6 shows the structure of a modification of the distance measuring unit 22 shown in FIG. 1. This modification utilizes the so-called sing around method commonly widely employed for the measurement of the velocity of sound in a substance. In FIG. 6, the structure and connection of the diode coupler 222, receiving circuit 223, gate 224 and peak detector 225 are similar to those shown in FIG. 2. The distance measuring unit 22 shown in FIG. 6 differs from that shown in FIG. 2 in that a pulse generator 232 generates its output signal by being triggered by the peak detection output signal of the peak detector 225. Also, in order that the transmitting signal generated from the pulse generator 232 may not mix in the detection output signal of the receiving circuit 223, and the peak detector 225 may not generate the trigger signal again immediately after the time of generation of the transmitting signal from the pulse generator 232, the peak detection output of the peak detector 225 is also applied to the gate 224 as an inhibit signal so that the detection output signal of the receiving circuit 223 may not pass through the gate 224 at that time. According to the structure shown in FIG. 6, the peak detector 225 generates the trigger signal with a period of $(\Delta t + \tau)$, where $\Delta t$ is the length of time required until, after generation of the transmitting pulse, the echo signal component from a region of interest is detected, and $\tau$ is the response delay time of the associated circuits. Therefore, each time the trigger signal is generated from the peak detector 225, this signal is converted into a voltage signal by an f/v converter 228, and this converted signal is stored in the memory 23 as a signal representing the distance L between the ultrasonic transducer 21 and the region of interest. Starting of the distance measurement and the reading of the distance signal from the f/v converter 228 in the manner described above are controlled by the controller 1.

Figure 7:
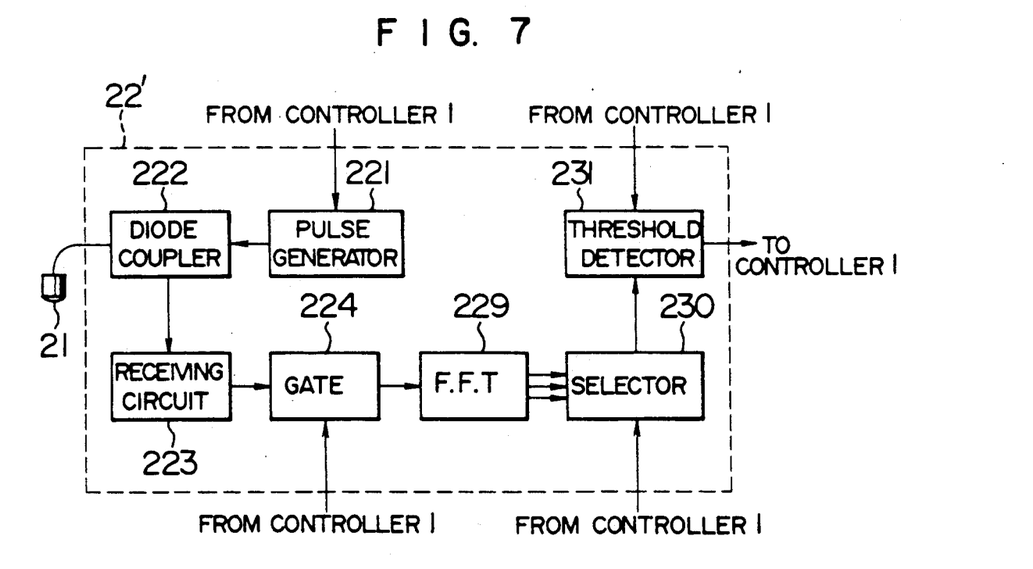

FIG. 7 shows the structure of a motion measuring unit 22' that can be used in lieu of the distance measuring unit 22 shown in FIG. 1. This motion measuring unit 22' utilizes the so-called pulsed Doppler method for monitoring the motion of a region of interest, for example, the wall or valve of the heart or blood in the heart. The motion measuring unit 22' is a modification of the distance measuring unit 22 shown in FIG. 2, and the pulse generator 221, diode coupler 222, receiving circuit 223 and gate 224 are similar to those shown in FIG. 2. Thus, the ultrasonic pulse wave is repeatedly transmitted from the ultrasonic transducer 21 toward the region of interest with the period T, and the echo wave reflected from the region of interest is received and detected by the receiving circuit 223. The detection output signal of the receiving circuit 223 is selected by the gate 224, and the selected echo signal is subjected to frequency analysis by a fast Fourier transformer 229. A selector 230 selects a desired frequency component among various frequency components of the output signal of the Fourier transformer 229, and the selected frequency component is applied to a threshold detector 231. When the amplitude of the selected frequency component exceeds a predetermined threshold level, the threshold detector 231 generates its detection output signal.

A Doppler shift corresponding to the moving velocity of the wave-reflecting region of interest occurs in the frequency of the echo signal. Therefore, when the amplitude of a certain frequency component of the signal subjected to the frequency analysis in the fast Fourier transformer 229 exceeds a predetermined level, this means that the wave-reflecting region of interest is in motion at a certain velocity. When the wall of the heart or blood in the heart is selected as the wave-reflecting region of interest, appearance of a detection output signal from the threshold detector 231 indicates a specific phase of the cardiac cycle. A procedure for obtaining an NMR image of the heart by the use of the motion measuring unit 22' shown in FIG. 7 will now be described. First, transmission of the ultrasonic pulse from the ultrasonic transducer 21 and the frequency analysis by the fast Fourier transformer 229 are repeated over more than one cardiac cycle so as to observe changes in the amplitudes of various frequency components of the echo signal due to the cardiac action. Then, the frequency component to be selected by the selector 230 and the threshold level of the threshold detector 231 are determined. Thereafter, prior to the excitation and measurement of the NMR signal in the step 5 in FIG. 4, measurement of the motion of the region of interest by transmission of the ultrasonic pulse from the ultrasonic transducer 21 (the frequency analysis of the detected echo signal by the fast Fourier transformer 239) is executed, and, instead of making the decision of the relation $\Delta L \leq \epsilon$ shown by the step 4 in FIG. 4, decision is made as to whether or not the threshold detector 231 generates its detection output signal. Only when the result of decision proves that the threshold detector 231 generates its detection output signal, the excitation and measurement of the NMR signal in the step 5 in FIG. 4 are executed while successively incrementing the value of n until the result of decision in the step 6 proves that n=N.

Figure 8A:
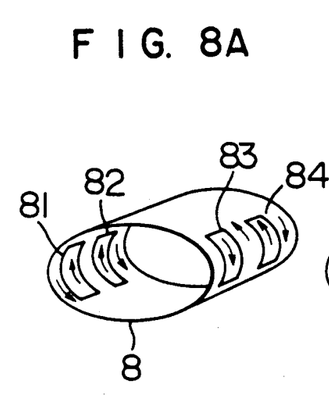
FIGS. 8A to 8C are perspective views showing various shapes respectively of the gradient coils used in the embodiment shown in FIG. 1.
Figure 8B:
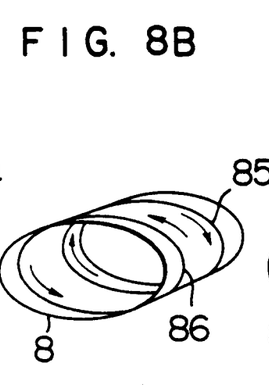
Figure 8C:
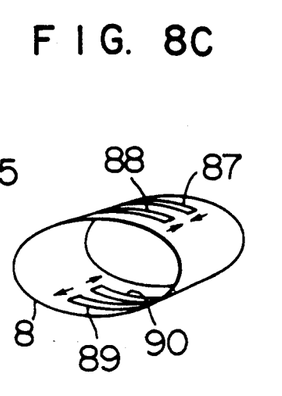

FIGS. 8A, 8B and 8C show the shape of the bobbin 8 and various forms of the gradient coils mounted on the bobbin 8 in the NMR gated imaging apparatus of the present invention shown in FIG. 1. This bobbin 8 has an elliptical sectional shape conforming to the sectional shape of a human body inserted into its internal cavity. Four coils 81 to 84 having a saddle shape as shown in FIG. 8A produce the x-direction magnetic field gradient $G_x$. Two annular coils 85 and 86 shown in FIG. 8B produce the z-direction magnetic field gradient $G_z$. Four saddle-shape coils 87 to 90 shown in FIG. 8C produce the y-direction magnetic field gradient $G_y$. In each of FIGS. 8A to 8C, the coils are formed along the elliptical outer surface of the bobbin 8 so that they exhibit high current-field conversion efficiency. Therefore, the condition required for the coil drivers 11 to 13 can be alleviated even in the case of imaging of the heart although fast driving of the gradient coils is required in such a case. The upper part and the bottom part of the bobbin 8 may be made flat to conform to the shape of a human body more tightly and to attain a high current-field conversion efficiency.

The aforementioned embodiments of the present invention have referred, by way of example, to blurring-free imaging of a moving region of interest in a human body, such as, the wall of the heart moving with the cardiac action. However, according to the present invention, gated imaging of a region of interest of an object can be made while monitoring the position of the region of interest itself. Therefore, it is apparent that the present invention is applicable not only to blurring-free imaging of a region of interest moving with the cardiac action but also to blurring-free imaging of the lung or the diaphragm making periodic motion with the breathing.

We claim:

1. An NMR gated imaging apparatus for obtaining an NMR image of an object placed in a space to which a static magnetic field is applied, the apparatus comprising:

means including an ultrasonic transducer positioned proximate to a surface of the object for repeatedly measuring a distance between the ultrasonic transducer and a region of interest in the object for more than one cycle of cyclic motion of the region of interest, the distance measuring means including means for transmitting an ultrasonic pulse signal from the ultrasonic transducer toward the region of interest and for detecting a time difference between a time of transmission of the ultrasonic pulse signal and a time of detection of an echo signal reflected from the region of interest as a distance measurement;

means for selecting and storing a value of distance between the ultrasonic transducer and the region of interest representing a predetermined position of the region of interest at which the region of interest is to be imaged;

means for effecting reaped NMR signal measurement of the region of interest including means for exciting spins in the object, gradient field applying means for applying gradient fields to the static magnetic field including first field gradient means for applying a first field gradient of one of a plurality of intensities to the static magnetic field, and second field gradient means for applying a second field gradient to the static magnetic field, and means for detecting an NMR signal from the object when the second field gradient is applied to the static magnetic field;

control means for controlling the distance measurement means and the NMR signal measurement means, the control means including comparison means for determining that a difference between the stored value of distance and the detected distance measurement is within a predetermined range, the control means alternately enabling the distance measuring means and the NMR signal measurement means so that the distance measurement and effected after completion of NMR signal measurement and NMR signal measurement is effected only when the difference between the stored value of distance and the detected distance measurement is within the predetermined range, the control means controlling the first field gradient means to change the one of the plurality of intensities to another of the plurality of intensities during repeated NMR signal measurement; and means for reconstructing an NMR image from at least one detected NMR signal.

2. An NMR gated imaging apparatus according to claim 1, wherein the control means enables stepwise change of the intensities of the first field gradient during the repeated NMR signal measurement.

3. An NMR gated imaging apparatus according to claim 1, wherein the ultrasonic transducer includes a piezoelectric polymer material.

4. An NMR gated imaging apparatus according to claim 1, wherein the distance measurement means includes time gate means and the control means controls the time gate means to enable passage of a selected echo signal therethrough.

5. An NMR gated imaging method for obtaining an NMR image of an object placed in a space to which a static magnetic field is applied, the method comprising the steps of:

repeatedly measuring distance between an ultrasonic transducer positioned proximate to a surface of the object and a region of interest in the object for more than one cycle of cyclic motion of the region of interest including transmitting an ultrasonic pulse signal from the ultrasonic transducer toward the region of interest and detecting a time difference between a time of transmission of the ultrasonic pulse signal and a time of detection of an echo signal reflected from the region of interest as a distance measurement;

selecting and storing a value of distance between the ultrasonic transducer and the region of interest representing a predetermined position of the region of interest at which the region of interest is to be imaged;

alternately effecting measurement of distance and NMR signal measurement wherein the step of NMR signal measurement includes exciting spins in the object, applying gradient fields to the static magnetic field including at least applying a first field gradient of one of a plurality of intensities to the static magnetic field and applying a second field gradient to the static magnetic field, and detecting an NMR signal from the object when the second field gradient is applied to the static magnetic field;

controlling the distance measurement and the NMR signal measurement alternately so that distance measurement is effected after completion of NMR signal measurement and NMR signal measurement is effected only when a difference between the stored value of distance and the detected distance measurement is within a predetermined range;

repeating the alternate execution of the distance measurement and the NMR signal measurement and changing the intensity of the first field gradient from the one of the plurality of intensities to another of the plurality of intensities during the repetition of the NMR signal measurement; and reconstructing an NMR image from at least one detected NMR signal.

6. An NMR gated imaging method according to claim 5, wherein the changing of intensity of the first field gradient during the repeated NMR signal measurement includes a stepwise changing of intensity.

7. An NMR gated imaging method according to claim 5, wherein the ultrasonic transducer includes a piezoelectric polymer material.

8. An NMR gated imaging method according to claim 5, wherein the steps of controlling and distance measurement include controlling a time gate to enable passage of a selected echo signal therethrough for distance measurement.

* * * * *